(12) United States Patent
Berger et al.

(10) Patent No.: US 8,419,936 B2
(45) Date of Patent: Apr. 16, 2013

(54) LOW NOISE BACK PRESSURE REGULATOR FOR SUPERCRITICAL FLUID CHROMATOGRAPHY

(75) Inventors: Terry A. Berger, Englewood, FL (US); Samuel Colgate, Gainsville, FL (US); Michael Casale, Hockessin, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 454 days.

(21) Appl. No.: 12/730,223

(22) Filed: Mar. 23, 2010

(65) Prior Publication Data

US 2011/0233299 A1   Sep. 29, 2011

(51) Int. Cl.
*B01D 15/08* (2006.01)

(52) U.S. Cl.
USPC ......... 210/198.2; 210/656; 210/137; 210/143

(58) Field of Classification Search .................. 210/635, 210/656, 659, 137, 143, 198.2; 95/82; 96/101; 422/70; 436/161
See application file for complete search history.

(56) References Cited

U.S. PATENT DOCUMENTS

| | | |
|---|---|---|
| 2,943,844 A | 7/1960 | Gustofson |
| 3,374,607 A | 3/1968 | Fisher |
| 4,042,326 A | 8/1977 | Kallos |
| 4,095,472 A | 6/1978 | Mowery |
| 4,373,864 A | 2/1983 | Massey |
| 4,478,720 A | 10/1984 | Perrut |
| 4,599,049 A | 7/1986 | Gordon |
| 4,624,625 A | 11/1986 | Schrenker |
| 4,690,689 A | 9/1987 | Malcosky |
| 4,814,089 A | 3/1989 | Kumar |
| 4,845,985 A | 7/1989 | Berger |
| 4,850,806 A | 7/1989 | Morgan |
| 4,880,543 A | 11/1989 | Khosah |
| 4,883,409 A | 11/1989 | Strohmeier |
| 4,892,654 A | 1/1990 | Nickerson |
| 4,962,662 A | 10/1990 | Berger |
| 4,990,076 A | 2/1991 | Lynch |
| 5,009,778 A | 4/1991 | Nickerson |
| 5,065,789 A | 11/1991 | Eslinger |
| 5,087,360 A | 2/1992 | Wright |
| 5,089,124 A | 2/1992 | Mahar |

(Continued)

FOREIGN PATENT DOCUMENTS

DE       2843920 A    10/1980

OTHER PUBLICATIONS

PCT/US 09/48906 International Search Report Oct. 19, 2009.

(Continued)

*Primary Examiner* — Ernest G Therkorn (57) ABSTRACT

A drive mechanism for back pressure regulator used in liquid chromatography, supercritical fluid chromatography, or supercritical fluid extraction allows very fine automated control over a very wide range of pressures by combining a linear actuator compressing a spring, pushing a pin. The nozzle assembly of the regulator comprises a flow through chamber containing a diaphragm and a seat, in which the pin pushes the diaphragm against the seat, together with an upstream pressure sensor and electronic feedback control to the motor of the actuator. The BPR of the embodiments exhibits high pressure stability and extremely low pressure noise, even at moderate to high pressures. The exemplary BPR can be use at either constant pressure or to generate pressure programs where the pressure is varied versus time. Further, the nozzle assembly has a field-replaceable head, requiring no mechanical adjustment on replacement.

6 Claims, 10 Drawing Sheets

U.S. PATENT DOCUMENTS

| | | | |
|---|---|---|---|
| 5,094,741 | A | 3/1992 | Frank |
| 5,108,264 | A | 4/1992 | Abdel-Rahman |
| 5,139,681 | A | 8/1992 | Cortes |
| 5,151,178 | A | 9/1992 | Nickerson |
| 5,151,250 | A | 9/1992 | Conrad |
| 5,178,767 | A | 1/1993 | Nickerson |
| 5,198,115 | A | 3/1993 | Stalling |
| 5,234,599 | A | 8/1993 | Cortes |
| 5,240,603 | A | 8/1993 | Frank |
| 5,281,406 | A | 1/1994 | Stalling |
| 5,305,232 | A | 4/1994 | Chimowitz |
| 5,322,627 | A | 6/1994 | Berger |
| 5,340,476 | A | 8/1994 | Berger |
| 5,344,311 | A | 9/1994 | Black |
| 5,346,622 | A | 9/1994 | Klee |
| 5,360,320 | A | 11/1994 | Jameson |
| 5,378,229 | A | 1/1995 | Layer |
| 5,403,089 | A | 4/1995 | Kuo |
| 5,431,545 | A | 7/1995 | Knight |
| 5,458,783 | A | 10/1995 | Levy |
| 5,462,431 | A | 10/1995 | Ahmady |
| 5,584,989 | A | 12/1996 | Jameson |
| 5,601,707 | A | 2/1997 | Clay |
| 5,614,089 | A | 3/1997 | Allington |
| 5,620,663 | A | 4/1997 | Aysta |
| 5,630,706 | A | 5/1997 | Yang |
| 5,653,876 | A | 8/1997 | Funke |
| 5,653,884 | A | 8/1997 | Smart |
| 5,716,525 | A | 2/1998 | Nickerson |
| 5,738,498 | A | 4/1998 | Allington |
| 5,755,559 | A | 5/1998 | Allington |
| 5,797,719 | A | 8/1998 | James |
| 5,843,311 | A | 12/1998 | Richter |
| 5,888,050 | A | 3/1999 | Fitzgerald |
| 5,996,818 | A | 12/1999 | Boje |
| 6,071,408 | A | 6/2000 | Allington |
| 6,162,022 | A | 12/2000 | Anderson |
| 6,183,635 | B1 | 2/2001 | Klee |
| 6,260,407 | B1 | 7/2001 | Petro et al. |
| 6,294,088 | B1 | 9/2001 | Allington |
| 6,309,541 | B1 | 10/2001 | Maiefski |
| 6,319,410 | B1 | 11/2001 | Allington |
| 6,345,528 | B2 | 2/2002 | Petro |
| 6,358,414 | B1 * | 3/2002 | Maiefski ................ 210/198.2 |
| 6,413,428 | B1 | 7/2002 | Berger |
| 6,450,146 | B1 | 9/2002 | Dickerson |
| 6,503,396 | B2 | 1/2003 | Kim |
| 6,558,540 | B2 | 5/2003 | Berger |
| 6,561,767 | B2 | 5/2003 | Berger |
| 6,632,353 | B2 | 10/2003 | Berger |
| 6,648,609 | B2 | 11/2003 | Berger |
| 6,652,240 | B2 | 11/2003 | Wichert |
| 6,652,753 | B2 | 11/2003 | Berger |
| 6,656,354 | B2 | 12/2003 | Berger |
| 6,685,828 | B2 | 2/2004 | Berger |
| 6,755,074 | B2 | 6/2004 | Davison |
| 6,923,916 | B1 | 8/2005 | Hiraku |
| 6,979,362 | B2 | 12/2005 | Jackson |
| 6,997,685 | B2 | 2/2006 | Lemmen |
| 7,048,517 | B2 | 5/2006 | Berger |
| 7,144,502 | B2 | 12/2006 | Fermier |
| 7,670,487 | B2 | 3/2010 | Wikfors |
| 7,905,133 | B2 | 3/2011 | Chordia |
| 7,964,029 | B2 | 6/2011 | Fogelman |
| 2002/0014106 | A1 | 2/2002 | Srinivasan |
| 2003/0054561 | A1 | 3/2003 | Gelernt |
| 2004/0018099 | A1 | 1/2004 | Berger |
| 2010/0040483 | A1 | 2/2010 | Berger |

OTHER PUBLICATIONS

Berger, Terry A.: Separation of polar solutes by packed column supercritical fluid chromatography, Journal of Chromatography, A 785 (1997) 3-33.

Berger, Terry A. and Blair K. Berger: Minimizing UV Noise in Supercritical Fluid Chromatography. I. Improving Back Pressure Regulator Noise, Journal of Chromatography A, 1218 (2011) 2320-2326 (Apr. 2011).

PCT International Search Report and Written Opinion of the International Searching Authority for PCT/US2011/041711 which is related to and has the same specification and claims as the present U.S. Appl. No. 12/730,223, and is assigned to the same assignee as the present application.

* cited by examiner

LOW NOISE BACK PRESSURE REGULATOR FOR SUPERCRITICAL FLUID CHROMATOGRAPHY

STATEMENT OF PRIORITY

None.

FIELD OF THE INVENTION

The present invention relates to methods and systems for controlling pressure of a mobile phase flowstream within chromatography and extraction systems, such as liquid chromatography, supercritical chromatography, and supercritical extraction systems, with a pressure regulator.

BACKGROUND

Supercritical fluid chromatography (SFC) is a separation technique similar to high performance liquid chromatography (HPLC), except one of the fluids used as a solvent is a highly compressible liquefied gas. Supercritical fluid extraction (SFE) is a related technique but with somewhat lower requirements for accurate flow or pressure control. The most common fluid used in SFC (and SFE) is carbon dioxide, which will be considered as representative of all such fluids.

At room temperature and atmospheric pressure, carbon dioxide is a low density gas (density approximately 0.002 g/cm3). The desirable characteristics of carbon dioxide for SFC and SFE are only achieved when the carbon dioxide is held at a liquid-like density, usually between 0.6 and 1.0 g-cm-3, by raising it's pressure to 80 to 600 Bar, while keeping the temperature in the general range of 20° to 100° C., and more commonly between 35 to 60° C. Under such conditions, the carbon dioxide: 1.) acts as a solvent, 2.) exhibits very high solute binary diffusion coefficients (allows higher flow rates than in HPLC), and 3.) exhibits very low viscosity (generates lower pressure drops across columns compared to HPLC).

To be useful in SFC (or SFE), the carbon dioxide is compressed to high pressures and pumped as a liquid or as a supercritical fluid, at a liquid like density, through a separation column. To prevent it from expanding to atmospheric pressure in the column, a back pressure regulator (BPR) is placed downstream of the separation column to keep the column outlet pressure above typically 80 Bar. Detectors capable of operating under high pressure may be mounted between the column and the BPR. Low pressure detectors may be mounted in the flow stream directly downstream of the BPR.

The pressure drops to near atmospheric pressure as it passes through the BPR. Both the BPR, and the fluid are cooled by the adiabatic expansion of the fluid. If pure carbon dioxide is used, it can actually form "dry ice" and intermittently plug the flow path, if external heat is not applied. Plugging and subsequent thawing results in intermittent, noisy flow, and loss of pressure/flow control. With modified fluids (where small amounts of other fluids are mixed with the carbon dioxide), "slush" of partially frozen carbon dioxide and modifier sometimes forms, causing the BPR to sputter, and loose pressure/flow control. Consequently, all BPR's used in SFC have been heated to maintain smooth flow control. Intermittent heating, such as performed by on-off heater controllers, can cause serious pressure instability. The heater control must be carefully optimized to avoid inducing pressure oscillations. With low levels of heating, the plugging problem can be avoided, but water from the atmosphere often condenses on the outlet line of the BPR. This liquid water, or sometimes ice, can cause multiple additional problems, and needs to be controlled/eliminated. Heating the BPR to a higher temperature eliminates the condensation/ice formation problem. However, the use of excessively high temperatures could damage thermally labile compounds passing through the BPR and need to be avoided.

In order to be appropriate for use in SFC, a BPR must be stable, accurate and repeatable, with appropriately low, unswept volume, and generate low UV detector noise. In addition it should be relatively inexpensive and easy to use and maintain. Users sometimes program pressure versus time, making electromechanical control desirable. As equipment has become more and more computer controlled, it has become desirable to have all the set points stored and downloaded from a single electronic method file, making electromechanical control of the BPR even more desirable.

Pressure affects retention and selectivity in SFC, although not very strongly, particularly when modified mobile phases are used. If the pressure drifts or wanders, retention times will drift and wander. Validating a method on a single instrument in a single lab requires reasonable pressure stability. In general, a series of injections must have retention time reproducibility less than +/−1%. Transferring methods from one lab to another requires reasonable pressure accuracy.

Standard mechanical back pressure regulators, such as those available from Tescom, generally have a large surface in direct contact with the fluid being controlled, which allows smoother, more precise control. However the internal volume of such devices is often very large, making them incompatible with some applications of SFC. Mechanical regulators often have as much as 5 mls of poorly swept internal volume. On the analytical scale, using 5 μm particles, on a 4.6 mm ID column, the volume containing a peak is roughly 75 to 200 μL. Any component in the flow path should have a dead volume roughly ⅓th these volumes or smaller, and the volume should be well swept, if the user expects to retain the separation (resolution between peaks) during decompression through the BPR. If the user wishes to place a detector downstream of the BPR, the volume of the BPR must be no larger than 10 to 40 μL, and preferably on the lowest end of this range. Unfortunately, the smaller the volume of the BPR the more difficult it is to control the pressure.

Mechanical BPR's, with large internal volumes, may be adequate for preparative and even semi-preparative scale SFC. On the preparative scale, samples are contained in 10's to 100's of mls of mobile phase. The BPR should have an inner volume less than ⅓th the volume containing the peak.

UV detectors are the most common detector type used in SFC. UV detector response is affected by refractive index changes in the mobile phase. The refractive index of carbon dioxide is highly dependent on temperature and pressure. In the past, the most common outlet pressure used in SFC has been 100 Bar. The most common column temperature used in SFC has been 40° C. At 40° C. the refractive index changes from 1.1120 at 90 Bar to 1.1606 at 110 Bar, a change of over 4%. This represents a change of approximately 0.2%/Bar. Oscillations in refractive index cause the light beam passing through a UV detector cell to be bent a variable amount. Pressure fluxuations generate refractive index fluxuations which causes variations in the light hitting the photosensitive portion of the detector. It is desirable to minimize pressure fluxuations to achieve low UV detector noise.

Prior back pressure regulator designs have proven to be temperamental in terms of both control and/or calibration for a specified range function. What is needed is device that dramatically reduces calibration requirements while maintaining dramatically improved control.

SUMMARY OF THE INVENTION

The preferred and alternative embodiments of the present invention disclose a drive mechanism for a back pressure regulator used in liquid chromatography, supercritical fluid chromatography, or supercritical fluid extraction allows very fine automated control over a very wide range of pressures by combining a linear actuator compressing a spring, pushing a pin. The nozzle assembly of the regulator comprises a flow through chamber containing a diaphragm and a seat, in which the pin pushes the diaphragm against the seat, together with an upstream pressure sensor and electronic feedback control to the motor of the actuator. The BPR of the embodiments exhibits high pressure stability and extremely low pressure noise, even at moderate to high pressures. The exemplary BPR can be use at either constant pressure or to generate pressure programs where the pressure is varied versus time. Further, the nozzle assembly has a field-replaceable head, requiring no mechanical adjustment on replacement.

The embodiments of the invention include a modular back pressure control system for supercritical fluid chromatography flow streams that allow interchange of any of the principal control elements without the need for recalibration of the device. After a single calibration of the system at the factory to compensate for electronic offsets and signal range, principal components including a micropositioning drive and a variable restriction nozzle cartridge may be interchanged at will to provide pressure regulation in excess of 400 bar. A high precision pressure sensor is used to assist in controlling the operatin of the micropositioning drive. Further, the precision of control of the regulator system can exceed typical commercial offerings by more than an order of magnitude in the critical low flow range of 0.5 to 10 mL/min that is most commonly associated with analytical flow rates in SFC and SFE.

The system depends on high precision registration of only four surfaces of the assembly—two on the micropositioning drive element to enforce the exposed length and end of travel limit for the end effector and two within the valve cartridge body itself to set the range of variability for the valve control. All of the surfaces are controlled simply by high precision machining tolerances and require only specified torque adjustment ranges to bring the surfaces into adequate proximity. As a result the manual assembly of the backpressure regulation system is dramatically simplified and robust.

The preferred and alternative embodiments of the present invention as mentioned above, includes a micropositioning drive, which may be controlled mechanically, hydraulically, thermally or electromagnetically. The critical requirement is that positional control of the drive at its end effector can be controlled in displacement steps of at most a few tenths of microns per bar of pressure change. This is best achieved by converting mechanical movement of the drive to a continuous force at the end effector. As practical matter it is highly desirable to achieve control of the end force at resolutions of tenths to hundredths of bars at the minimum step change.

In the preferred embodiment an electric stepper motor type linear actuator is used to drive a pair of thrust elements in communication with a high force constant spring. The spring attenuates relatively large displacement steps of the stepper motor at a determined rate of force per displacement. The distant thrust element is placed in communication with the drive end effector, in this case a machined metal pin, and the pin movement interacts with the nozzle cartridge to produce a pressure change. Alternative means of supplying constant force to the drive end effector may include use of constant force motors, solenoids, and hydraulic or pneumatic control systems. The drive system must be rapid enough to respond to significant pressure changes caused by rapid variations in viscosity and flow of the control system.

DETAILED DESCRIPTION OF THE INVENTION

Figure 1:
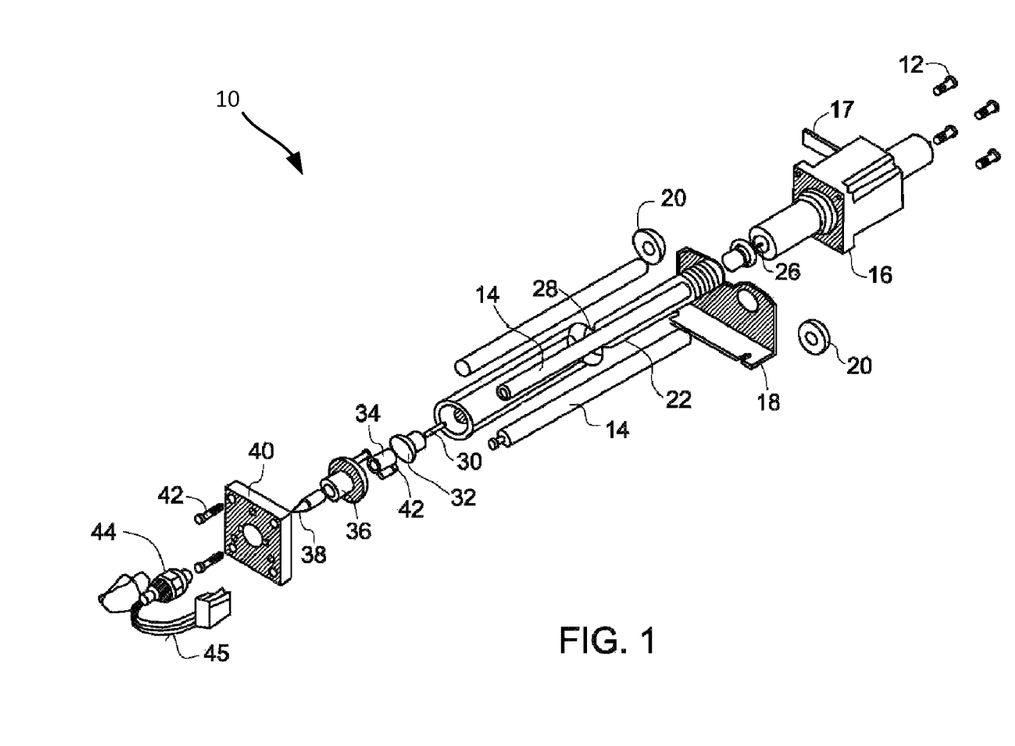
FIG. 1 is an isometric diagram of an exemplary back pressure regulator of the embodiments.
Figure 2:
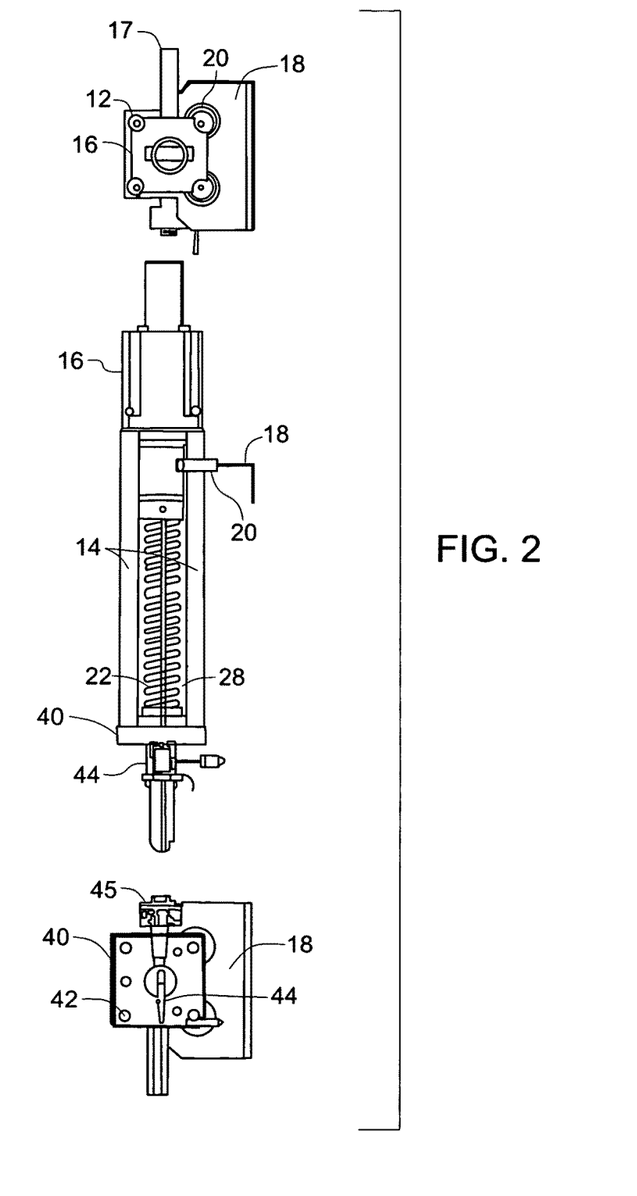
FIG. 2 illustrates side and end views of the back pressure regulator of FIG. 1.

Referring to FIG. 1, a preferred embodiment of a back pressure regulator (BPR) assembly 10 for use in chromatographic or extraction systems such as supercritical chromatography systems is illustrated in an exploded isometric view. FIG. 2 illustrates side, rear end, and front end views of assembled BPR 10. Mounting screws attach each of four tie rods 14 to a mounting plate on stepper motor 16 having electronic controls via connection 17. BPR mounting bracket 18 provides a mounting surface for the BPR to an external housing via grommets that slide onto two of the tie rods 14. Rear spring thrust element 24 is received by rear end of modified high force spring 22 and receives an actuating lead screw or pin 26 from motor 16. A cylindrical spring guide 28 houses spring 22 within a framework of tie rods 14. At front end of spring 22, screw 30 is connected to front spring thrust element 32. Bushing 34 is received into a cylindrical protrusion of nozzle mount plate 36. Nozzle pin 38 is also received through nozzle mount plate 36 by bushing 34. Mount plate 36 connects to front plate 40 using screws 42 or other equivalent connectors. Screws 42 connect front plate 40 to ends of tie rods 14. Heated nozzle assembly 44 is held near to nozzle pin 38 to complete the BPR assembly. Electronic controller connector 45 provides computer controls and monitoring of assembly 44.

Figure 3:
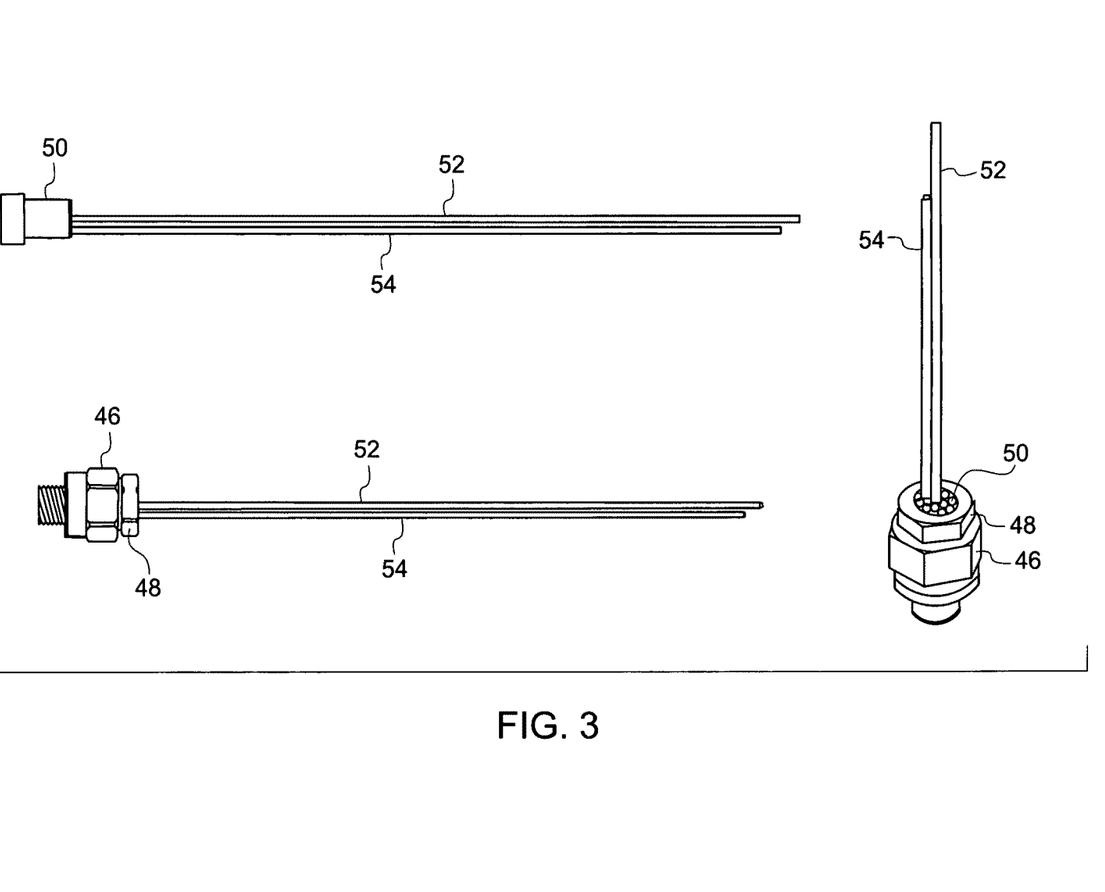
FIG. 3 illustrates various views of the nozzle assembly of the embodiments.

Referring to FIG. 3, various views of the exemplary heated nozzle assembly 44 with flow tubes are illustrated. Central to Nozzle assembly 44 is Nozzle insert assembly 50 comprises nozzle insert 56 which receives outlet flow tube 52 through its radial center point. Inlet flow tube 54 is offset from insert 50 but parallels outlet tube 52. Inlet tube transfers flow into inlet channel 53 and outlet tube 52 provides an exit path for flow through outlet channel 51. Nozzle insert assembly 50 additionally comprises a machined seat 56 that together with inlet tube 54 and outlet tube 52 form a brazed assembly. Nozzle insert 50 contains an annular ring 57 that insets nozzle seat 56 relative to an external edge. Annular ring 57 is in fluidic communication with nozzle inlet tube 54. Nozzle seat 56 is in fluidic communication with, and provides an entrance to nozzle outlet tube 52. In one embodiment, an internal diameter for inlet channel 53 is 0.020 inches and an internal diameter for outlet channel 51 is 0.040 inches, however these dimensions are merely exemplary and may vary higher or lower.

Figure 4:
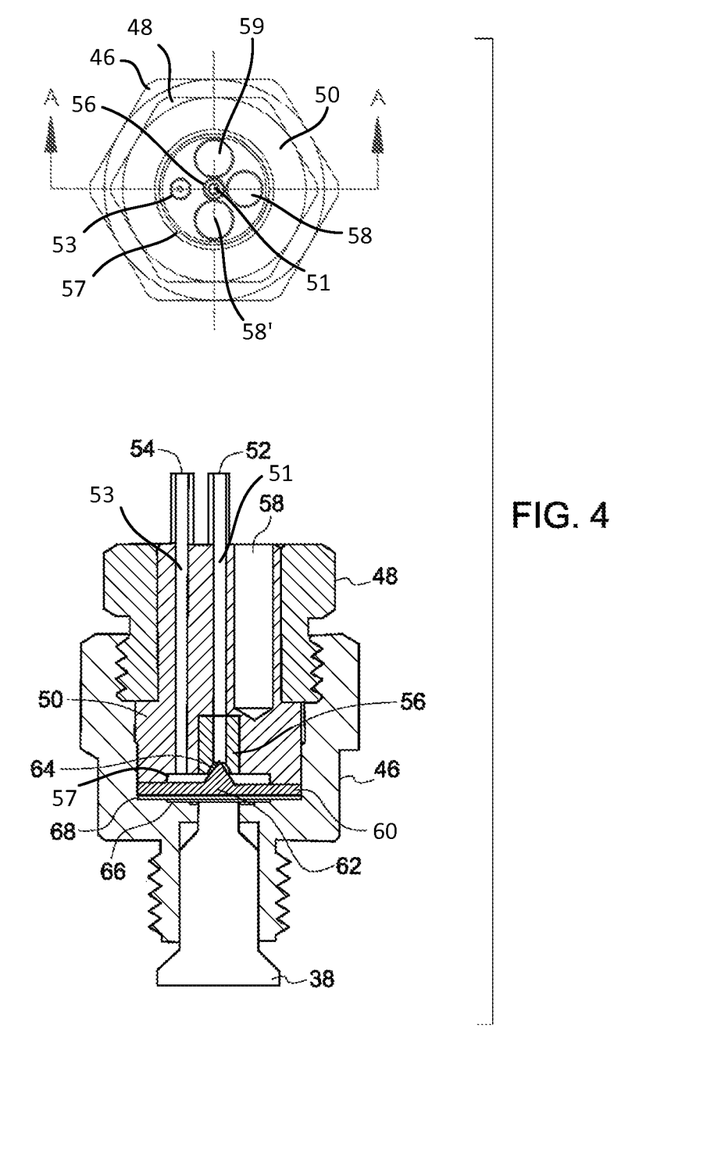
FIG. 4 illustrates a plan and cross-sectional view of the nozzle assembly of the embodiments.

FIG. 4 illustrates more detailed plan and cross-sectional views of exemplary nozzle assembly 44. Nozzle body 46 receives nozzle nut 48 with a threaded connection that extends only partially into internal area of body 46. Outlet channel 51 receives outlet flow tube 52 through the nozzle insert's radial center point. Inlet flow channel 53 is offset from seat 56 but parallels outlet channel 51.

Figure 5:
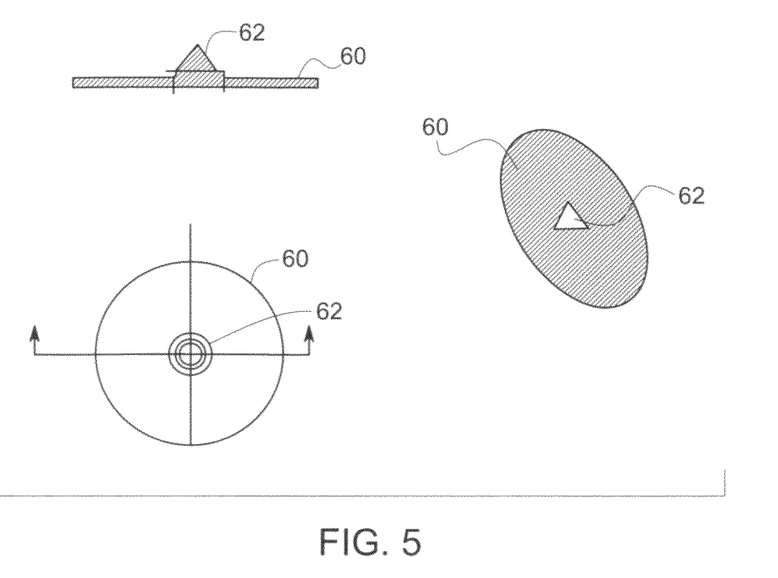
FIG. 5 illustrates various views of a diaphragm for the nozzle assembly of the embodiments.
Figure 6:
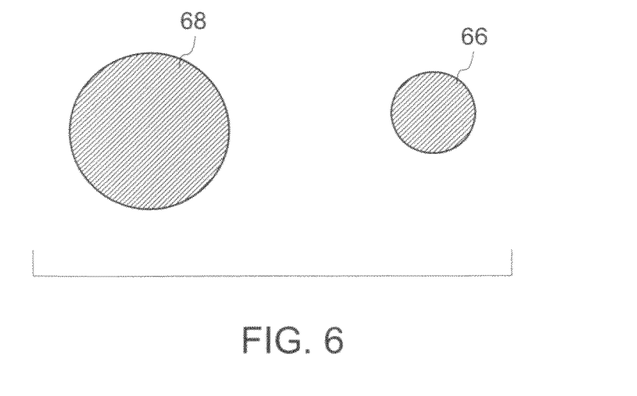
FIG. 6 illustrates plan views of shims used in the nozzle assembly of the embodiments.

Nozzle diaphragm 60 is positioned adjacent to nozzle insert 50 such that a conical or raised feature 62 (see FIG. 5) is substantively coaxial to and partially contained within nozzle seat 56. Nozzle diaphragm 60 is backed by spring shims 68 and 66 (see FIG. 6) in a parallel and coaxial arrangement. In FIG. 6, shims 66 and 68 are thin, circular, metallic discs. Shim 66 can have an exemplary dimension of 0.313× 0.005 inches and shim 68 can have larger exemplary dimension of 0.5×0.005 inches. As one skilled in the art recognizes, these dimensions are merely for illustration of the embodiments and can vary larger or smaller without falling outside the scope of the present invention. Smaller diameter shim 66 is located between nozzle pin 38 and larger diameter shim 68 (and further diaphragm 60).

The spring shims 68 and 66 and diaphragm 60 are constrained by nozzle body 46 and the nozzle insert 50. The surface of nozzle body 46 adjacent to spring shim 66 may be angularly recessed relative to an undeflected, planar spring shim.

Nozzle nut 48 applies compressive force against nozzle insert 50 and nozzle body 46 such that a high pressure seal is made between the faces of nozzle diaphragm 60 and the surface of nozzle insert 50. Exemplary nozzle insert 50 further contains two electric cartridge heaters 58 and a resistive temperature sensor 59. Nozzle pin 38, provides a motive force against spring shims 68, 66 and diaphragm 60.

Heating element 58 is located axially within insert assembly 50 and preferably is located near to, but does not directly contact, inlet tube 54, outlet tube 52, nozzle seat 56 or any side or lower surfaces of nozzle body 46 and nozzle nut 48, however contact with the aforementioned nozzle assembly parts will not cause degradation in performance of the nozzle assembly 50. Up to two heating elements 58, 58' are illustrated in plan view. A temperature sensor 59, is also positioned parallel to heating elements 58 and 58'.

In operation of the preferred and alternative embodiments of BPR 10, a fluid enters the nozzle via nozzle inlet tube 54. Said fluid, additionally contained within annular ring 57 may provide pressure against the interior diaphragm 60 surface. Said pressure will provide force against, and may cause deflection of diaphragm 60 which is circumferentially constrained by nozzle body 46 and nozzle insert 50. Such deflection force is opposed by spring shims 68 and 66 which additionally prevent non-axial deflection of the diaphragm. Deflection of the diaphragm 60 away from nozzle seat 56 opens the nozzle to allow increased flow to outlet channel 51 and tube 52. Deflection of the nozzle diaphragm 60 towards nozzle seat 56 decreases flow.

Motive force on nozzle pin 38 can be provided to further oppose deflection pressure on the diaphragm 60. Increased pressure on pin 38 can cause a forward (closing) movement of diaphragm 60 toward nozzle seat 56. Such forward motive force reduces fluid flow exiting via nozzle seat 56 and nozzle outlet tube 52. Reduced flow exiting the nozzle will provide for increased pressure within annular ring 57 which provides additional pressure on the interior surface of the diaphragm which opposes motive force on pin 38 until forces balance and a stable pressure is achieved.

Within the normal operating pressure of a supercritical fluid chromatograph, the pressure difference between the back pressure regulator and an ambient outlet vent will substantively exceed 100 bar. This pressure differential is that which is experienced by the fluidic escape. Such pressure difference causes state changes in escaping fluid from supercritical or dense liquid state to a gaseous state. This state change represents greater than a 50:1 increase in volume as the transition occurs. This expansion causes extensive evaporative cooling. In the preferred embodiment, heaters are provided for addition of heat to counteract the effects of expansive cooling. Contrary to existing prior art, the heaters are placed in direct thermal communication with the area of expansive cooling; i.e. the nozzle seat 56 and the nozzle outlet channel 51, and less directly heating the inlet tube 54 channel 53 and surface of annular ring 57 and thus providing additional heat to the fluid contained within. The direct addition of heat in these areas delays the rapid and significant cooling of the fluid until after the fluid exits the region in close proximity to the nozzle seat 56 and diaphragm conical feature 62.

Pin 38 or dimpled diaphragm 60 is pushed into an orifice 64 by compressed spring 22. The spring is compressed by a linear actuator comprised of stepper motor 16 and a lead screw 26. The linear actuator, by itself, does not possess adequate resolution to allow anything other than very crude pressure control. The linear actuator in the embodiments can move less than 0.0003 inches/step or 0.0076 mm/step. However, in one embodiment, the entire distance of travel from totally open to totally closed is on the order of 25 to 40 μm or 0.001 to 0.0016 inches. If the best linear resolution of the actuator is 0.0003 inches/step, there can only be three to seven different positions for controlling pressure over the range of 0-400 or 0-600 Bar. Since pressure control in an SFC system of less than +/−1 Bar is desired, the linear actuator alone cannot provide adequate resolution for optimal pressure control.

The use of the spring 22 allows very subtle variation in the force generated. By choosing a long spring 22 with a relatively modest spring force, each micro-step on the linear actuator represents a very small variation in force applied. One thousand steps produce 30 pounds of force, etc. In one embodiment, more than two inches of spring compression can produce more than 200 pounds of force. As an example, if the spring 22 has a spring constant of 100 pounds/inch, each step of 0.0003 inches represents 0.03 pound of force. Each step produces a miniscule amount of pressure perturbation. The very fine control represented by each step allows smooth changes in pressure without oscillations. Pressure can be programmed to produce very smooth pressure ramps. By using an inexpensive linear actuator, it provides the ability to control or program the outlet pressure of a chromatograph through computer control.

Further, the spring 22 dampens pressure fluxuation caused by other devices, such as reciprocating pumps mounted upstream of a separation column. Using the exemplary embodiments, short term (e.g., 5 Hz) pressure variations at the BPR 10 have been measured as low as 0.8 pounds per square inch (psi) with the BPR 10 controlling at 2900 psi with 3 ml/min of flow consisting of 20% methanol in carbon dioxide. This represents 200+/−0.03 Bar; <+/−0.02%, which is at least an order of magnitude better than any previously reported BPR used in SFC. This extremely low observed pressure noise significantly contributes to observed low UV detector noise.

In the preferred embodiment, nozzle assembly 44 uses dimpled diaphragm 60 pressed into a shaped orifice 64. The fluid from the column outlet enters a small chamber defined by the annular ring 57, diaphragm 60 and the orifice 64 through a tube 52, and exits through the orifice into another tube 54. There is no moving seal, but the diaphragm 60 flexes depending on the force applied. The internal volume of the device is less than 10 μL. The diaphragm 60 can require several hundred pounds of force to control at 400 Bar. In this case the force is provided by the drive mechanism described above. Since the stepper motor 16 is located some distance from the nozzle assembly 44 there is little to no heat transfer from the motor 16 to the nozzle assembly 44.

In one embodiment, nozzle body 46 is approximately one inch in outer diameter, yet it can accommodate two 25 Watt heaters that are one inch long as well, such as an exemplary platinum resistance temperature sensor. The temperature of nozzle assembly 44 is controlled by a purpose built electronic circuit with an optimized proportional, integral, differential (PID) control algorithm.

In the prior art, field replacement of a nozzle assembly required careful adjustment to work properly. The adjustment was required because a number of machined parts, each with its own tolerance were stacked together to create the nozzle assembly. In the present invention, all the stacked tolerances were individually eliminated, until a single part carried a single critical dimension. The tolerance on this dimension is within the range of adjustment possible using the electronic controls.

In an alternative embodiment, the pin 38 is tapered and passes through a seal before being pushed into the shaped orifice 64. Fluid enters through the same tube 52 attached to the column or UV detector outlet. The fluid is in contact with the moving seal around the spring and exits through the orifice of the seat 56 into another tube. The taper on the pin 38 produces a variable gap between the pin and orifice 64 and produces a controllable resistance to flow.

If power fails, the BPR 10 does not instantly lose control and become completely open. There is some remaining resistance to rotation by the motor 16 and lead screw 26. The force on the diagram 60 caused by the pressure in the column will gradually force the pin to retreat and the BPR will open. The slow decay in pressure prevents damage to fragile column packings, such as many chiral packings, which are very expensive to replace.

Figure 7:
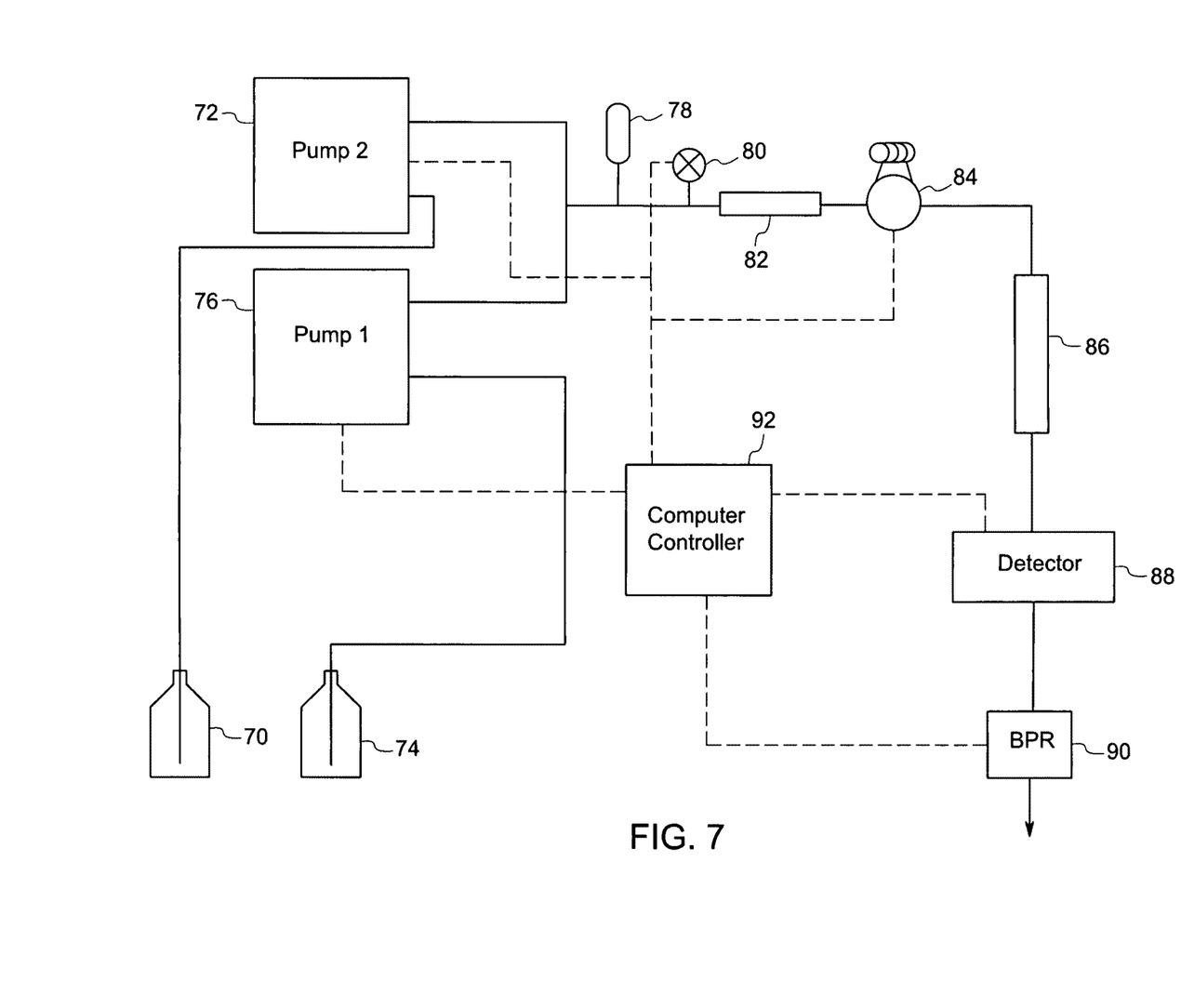
FIG. 7 is a supercritical fluid chromatography system that is capable of implementing the embodiments of the present invention.

FIG. 7 is a schematic of a modern binary High Performance Liquid Chromatography (HPLC) or SFC system capable of implementing the embodiments of the present invention. The system is comprised of a duplex pump 76 which receives a fluid supply [typically high purity water or carbon dioxide] from reservoir 74. A second duplex pump 72 typically receives an organic solvent of higher compressibility from reservoir 70. The two flow streams mix at a tee then continue past pulse dampener 78 and output pressure sensor 80 through diffusion tube 82. The mobile phase mobile phase flowstream continues to injector valve 190, which injects samples or chemical solutions for separation into the mobile phase. After injector valve 84, the mobile phase continues through stationary phase separation column 86, detector 88, and back pressure regulator 90, before being exhausted to waste or directed to another process such as fraction collection in preparative systems. Also shown in FIG. 7 is the computerized system controller 92 that directs the specific operation of the system, including elements of BPR 90, which in the specific embodiments is exemplary BPR 10.

In operation, each pump of the system of FIG. 7 is set to an initial flow rate to produce a specific composition of mobile phase. The mobile phase is allowed to equilibrate with the separation column. Detectors are adjusted to recognize the signal produced at this initial state as a "baseline" value. To begin an actual separation, the sample loop of injector valve 84 is filled with liquid containing a mixture of dissolved components. The valve is actuated to allow mobile phase to push the sample segment onto the separation column. Individual components of the sample mixture experience different retention times on the separation column and emerge at different times. The detector senses the components and generates an electronic signal different from the baseline value which can later be interpreted for component type and/or amount by the system controller. Back pressure regulator 90 provides sufficient backpressure to prevent disturbances in the detector from outgassing of mobile phase elements.

If the initial mobile phase composition is sufficient to separate all components of the sample in a timely manner, it is maintained over the separation period. This is referred to as isocratic separation. Frequently, the adsorption of some components of a sample is so strong that the initial flow composition would take inordinately long to elute the mixture. A technique called gradient elution is used in these cases. Gradient elution allows the sample application and initial separation of poorly retained components to occur at the initial condition, then ramps the solvent composition to higher concentration of the stronger solvent to elute more strongly retained components. At the same time, the flow of the weaker solvent of the binary mixture is reduced to maintain a constant total flow rate.

EXAMPLE

Figure 8:
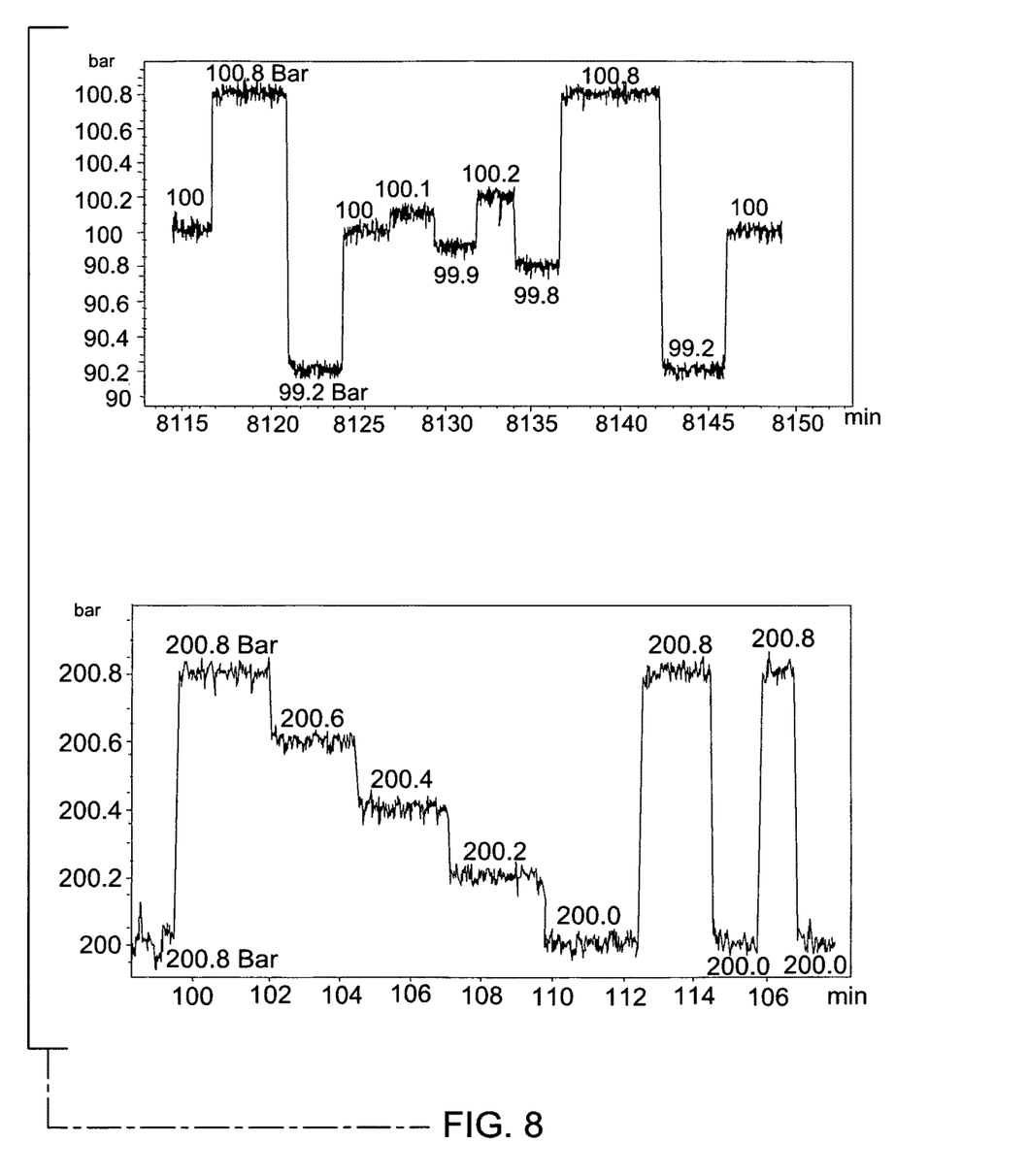
FIGS. 8, 9, 10, and 11 are graphs showing results of an operation of the embodiments.

The repeatability and peak to peak pressure noise of the BPR in the Fusion module was measured, at a frequency of 20 Hz, at 2.0 ml/min of 15% methanol, at 40° C. A 4.6×250 mm column packed with 5 μm silica particles helped dampen flow (and pressure) noise induced by the pumps. The pressure was stepped by as little as 0.1 Bar. The data in FIG. 8 show that pressure noise for this specific BPR is less than +/−0.05 Bar peak to peak at both 100 and 200 Bar, while the repeatability is <+/−0.02 Bar (<1 psi). Not all BPR's of this design perform this well.

The composition and flow rate were also changed while holding pressure constant at 150 Bar. The results, shown in FIG. 9, indicate no variation in either the absolute pressure value, deviation from the set point, or the peak to peak pressure noise, even though flow was varied from 1 to 4 ml/min, while the composition was varied from 5% to 40%. The sharp spikes in pressure between set points indicate the breakthrough times for the changes in modifier concentration. Such breakthrough causes a rapid change in viscosity. Automatic adjustment by the electronics to the new viscosity took a few seconds. These experiments were repeated at 100, 200, and 300 Bar. In all cases, $N_{p-p}$ p<+/−0.1 Bar.

Figure 9:
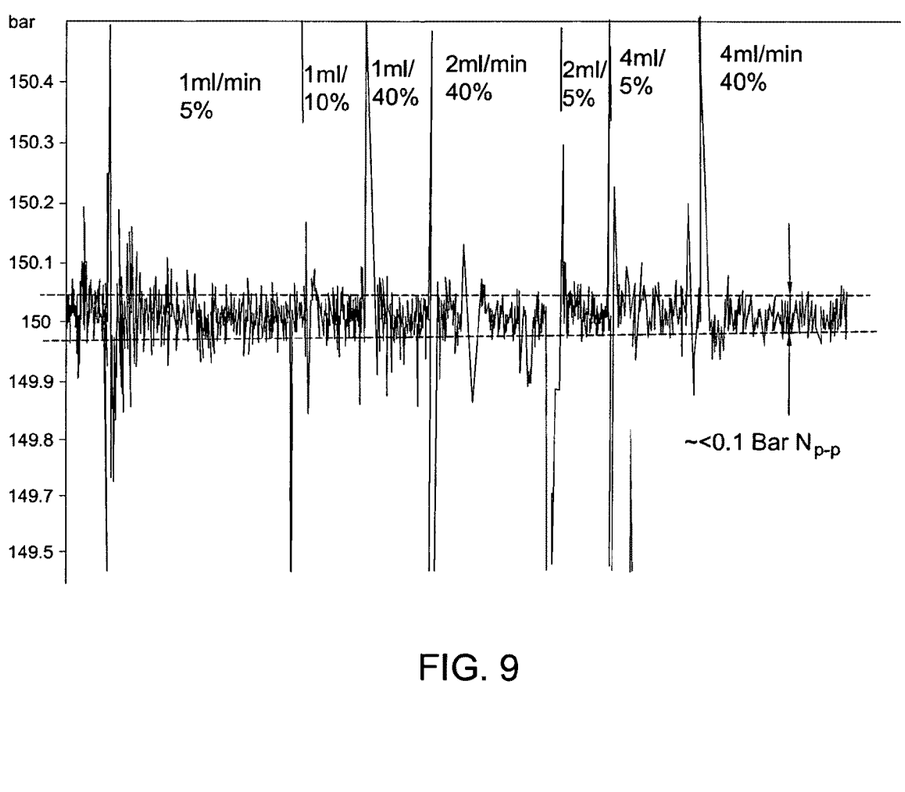

Since FIGS. 8 and 9 establish that the BPR is highly repeatable with very low pressure noise, the effect of larger changes in the system outlet pressure on UV detector offsets can be measured precisely. The UV diode array detector wavelength ($\lambda$) was set to 280 nm with a 16 nm bandwidth (BW). The reference wavelength ($\lambda_r$) was 360 nm with a 40 nm BW. The slit was set to 16 nm. The electronic filter was set to >0.1 min which corresponds to a 2.5 Hz data rate. UV spectra were monitored on-line to assure there was no absorbance at the wavelength used, so that all shifts in the baseline could be attributed to RI changes.

The system outlet pressure was manually changed approximately every 30-45 seconds, back and forth between each two sets of pressures, while the UV signal offset, caused by the pressure perturbation, was measured. At least three steps were made at each pair of pressures. The results from a typical set of measurements are presented in FIG. 10. The lower trace is the system outlet pressure, just downstream of the UV detector. From left to right, there are 3 steps from 120 to 140 bar (20 bar), 3 steps from 120 to 130 bar (10 Bar), 3 steps from 120 to 125 bar (5 Bar), 3 steps from 120 to 122 bar (2 Bar), and 3 steps from 120 to 121 (1 Bar). The steps are meant to emulate BPR $N_{p-p}$ of +/−10 Bar (20 Bar), +/−5 Bar (10 Bar), +/−2.5 Bar (5 Bar), +/−1 Bar (2 Bar), and +/−0.5 Bar (1 Bar).

Figure 10:
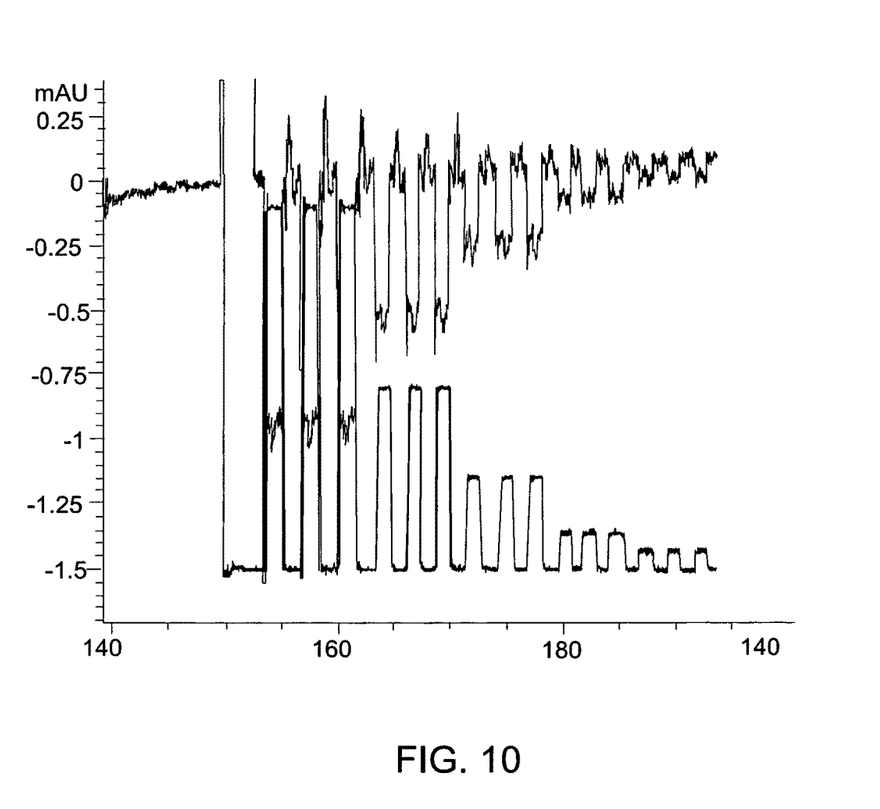

The upper trace in FIG. 10 shows the UV detector signal responding to the pressure steps. The amplitude of the steps is a direct measure of baseline offset caused by the pressure perturbations and ultimately by the change in the RI of the mobile phase with pressure. These measurements were repeated with the base pressure (the initial pressure) at 90, 100, 120, 140, and 200 Bar, with the 20, 10, 5, 2, and 1 Bar steps superimposed.

Screen captures of the results were printed and the approximate Np-p was manually measured with a caliper. The overall results are presented in FIG. 11. UV detector offsets were the largest in the regions where the RI (and density) changes the most with small changes in pressure, as expected. Operation at higher pressures resulted in decreased detector offsets and should also result in lower UV Np-p.

Figure 11:
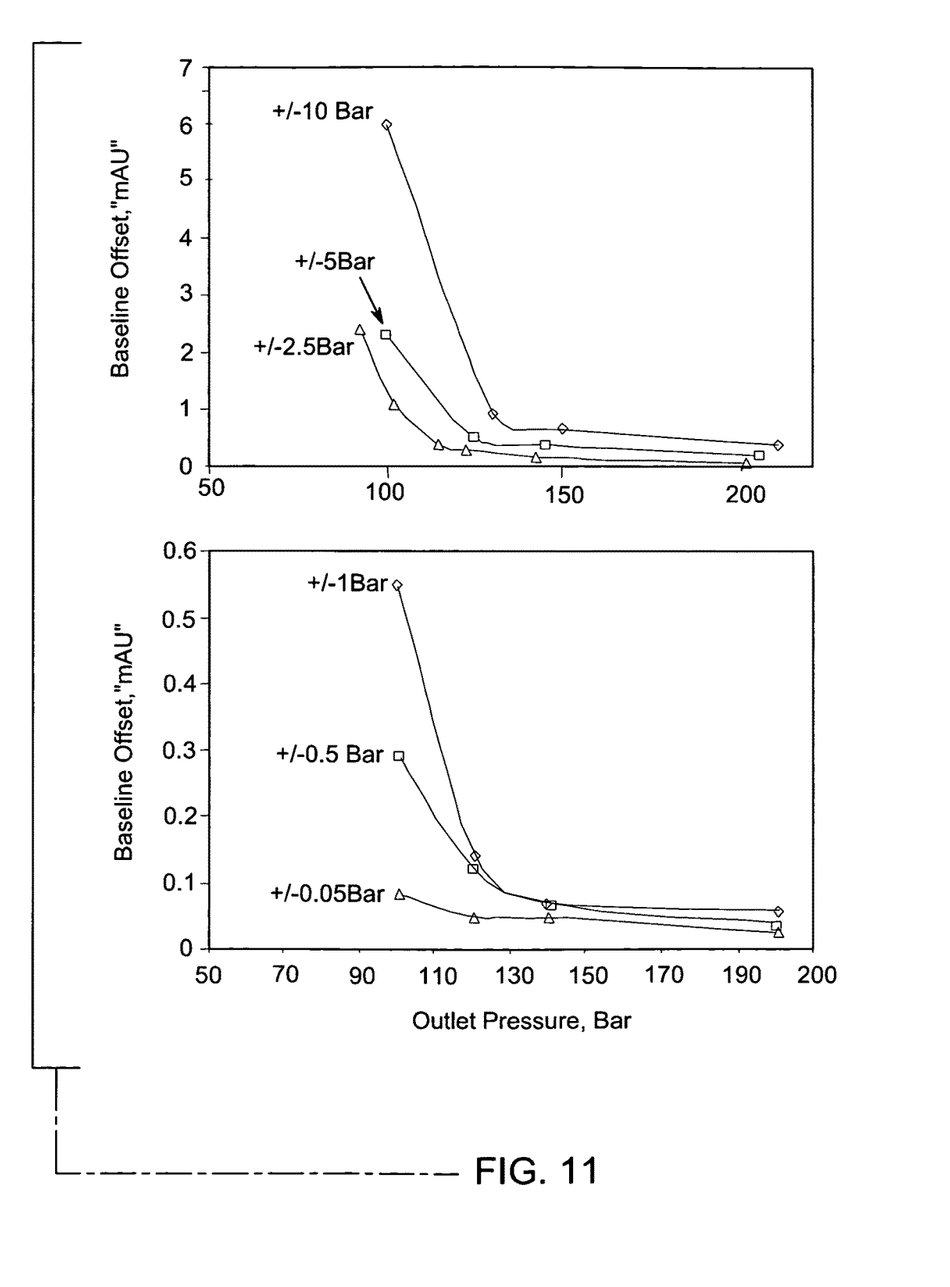

Larger perturbations (5-20 Bar), such as those in the upper graph of FIG. 11, will likely be caused only randomly or highly intermittently. As recently observed anecdotally, large pressure spikes cause significant spikes in the UV baseline. At 90 Bar, the 20 Bar steps to 110 Bar caused a >6 mAU (filter>0.1 min) change in the UV signal. Note that an increase in pressure, resulting in an increase in the RI, causes a decrease in the UV signal.

Some real BPR's generate as much as +/−2.5 Bar pressure noise, at moderate frequencies. One well known BPR, uses a solenoid to oscillate a pin into an orifice between 1 and 20 Hz turning flow on and off, to control pressure.

A typical peak widths are 0.05 to 0.2 min, on 5 μm particles requiring a minimum detector data rate of 1.25 to 5 Hz. Smaller particles generate narrower peaks and require higher detector frequencies. The data in FIG. 8 suggest BPR oscillations, at frequencies near peak frequencies, can generate baseline noise >1 mAU (filter >0.1 min), making trace analysis under such conditions problematic.

Until recently, the quietest reported BPR's used in SFC exhibited peak to peak pressure noise of ≈+/−0.5 Bar, but with heavy filtering on the signal. As indicated by the middle curve in the bottom of FIG. 11, this BPR should have been capable of producing UV noise of 0.3 mAU or less (with filter >0.1 min). An extensive search of the prior art shows 0.3 to 0.5 mAU noise using this BPR, but no better. The middle curve in the bottom of FIG. 11 suggests noise should improve to below 0.1 mAU at higher pressures, which was (almost) never previously observed.

The specific BPR used in the present tests has the lowest pressure noise reported in the SFC literature, by an order of magnitude. Its performance is indicated in FIGS. 8 and 9 and by the bottom curve in FIG. 10. Noise improved significantly at higher pressure, such as 200 Bar. However, even at 100 Bar, noise was very low, by historical standards Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A system for chromatography, comprising:
   a first pump for pumping a first relatively incompressible fluid flowstream;
   a second pump for pumping a second relatively compressible solvent fluid flowstream;
   mixing device that combines said first and second flowstreams;
   an injection device that can introduce samples or solutions into any of said flowstreams;
   a chromatography separation column, downstream of said mixing device and that can receive said combined flowstream;
   a detector, for detecting a concentration of a constituent in one of said flowstreams;
   a computer controller, directing certain operations of the system; and
   a back pressure regulator, located downstream of said column, wherein said back pressure regulator includes a device comprising a nozzle insert with an outlet flow channel that can receive an outlet flow and an inlet flow channel that can receive an inlet flow, and further includes a seat, connected near an end of said insert, inset from said nozzle insert such that said seat can be in fluidic communication with said outlet flow channel.

2. The system of claim 1, wherein said outlet flow channel is located near to center axis of said nozzle insert, and
   said inlet flow channel is located at a position offset from said outlet flow channel.

3. The system of claim 1, wherein the nozzle insert further comprises:
   a heating element arranged near to said outlet channel such that heat from said heating element can be in thermal communication with said outlet flow channel.

4. The system of claim 1, further comprising:
   a nozzle body at least partially receiving said nozzle insert and said seat; and
   a diaphragm having a first surface positioned adjacent to said seat wherein said nozzle body constrains a circumferential edge of said diaphragm.

5. The system of claim 4, further comprising:
   a shim element, positioned adjacent to a second surface of said diaphragm that is opposite to said first surface of said diaphragm that is adjacent to said seat.

6. The system of claim 4, further comprising:
   a linear actuator that can apply a force to the second surface of said diaphragm directly or through said shim, wherein said force can cause the first surface of the diaphragm to seal against an orifice of said outlet flow channel.

* * * * *